(12) United States Patent
Moller et al.

(10) Patent No.: US 7,476,377 B2
(45) Date of Patent: Jan. 13, 2009

(54) RUBIDIUM-82 GENERATOR BASED ON SODIUM NONATITANATE SUPPORT, AND IMPROVED SEPARATION METHODS FOR THE RECOVERY OF STRONTIUM-82 FROM IRRADIATED TARGETS

(75) Inventors: Teresia Moller, College Station, TX (US); Todd Adams, Franklin, TX (US); Alan Cisar, Cypress, TX (US); Hariprasad Gali, College Station, TX (US); Paul Sylvester, Waltham, MA (US)

(73) Assignee: Lynntech, Inc., College Station, TX (US)

( * ) Notice: Subject to any disclaimer, the term of this patent is extended or adjusted under 35 U.S.C. 154(b) by 876 days.

(21) Appl. No.: 10/894,870

(22) Filed: Jul. 19, 2004

(65) Prior Publication Data
US 2005/0058839 A1    Mar. 17, 2005

Related U.S. Application Data

(63) Continuation-in-part of application No. 09/922,353, filed on Aug. 2, 2001, now Pat. No. 6,908,598.

(51) Int. Cl.
*C01D 17/00* (2006.01)
(52) U.S. Cl. .......................... 423/598; 423/2; 423/249; 252/184; 502/400
(58) Field of Classification Search ................. 423/598, 423/2, 249; 502/400; 252/184
See application file for complete search history.

(56) References Cited

U.S. PATENT DOCUMENTS

| | | | |
|---|---|---|---|
| 3,953,567 A | 4/1976 | Grant et al. | |
| 3,957,945 A | 5/1976 | Grant et al. | |
| 4,276,267 A | 6/1981 | Bentley et al. | |
| 4,406,877 A | 9/1983 | Neirinckx et al. | |
| 4,562,829 A | 1/1986 | Bergner | |
| 4,585,009 A | 4/1986 | Barker et al. | |
| 4,597,951 A | 7/1986 | Gennaro et al. | |
| 5,167,938 A | 12/1992 | Heaton et al. | |
| 5,190,735 A | 3/1993 | Phillips et al. | |
| 5,296,203 A | 3/1994 | Phillips et al. | |
| 5,330,731 A | 7/1994 | Heaton et al. | |
| 5,885,925 A | 3/1999 | DeFilippi et al. | |
| 5,966,583 A | 10/1999 | Taylor et al. | |
| 5,989,434 A | 11/1999 | Lundquist et al. | |
| 6,106,799 A | 8/2000 | Lehto et al. | |

FOREIGN PATENT DOCUMENTS

EP        0 043 650      11/1981

WO        97/14652    *   4/1997

OTHER PUBLICATIONS

Yukio Yano, "Essentials of a Rudidium$^{82}$ Generator for Nuclear Medicine", 1987, Appl. Radiat. Isot. vol. 38. No. 3. pp. 205-211.

Y. Yano, T. F. Budinger, J L. Cahoon, and R H Huesman, "An Automated Microprocessor-Controlled Rb-82 Generator for Positron Emission Tomography Studies", ©1984, pp. 97-122.

Furn F. Knap, Jr., Thomas A Butler, "New Systems for Nuclear Medicine Applications", ACS Symposium Series 241, Radionuclide Generators, Mar. 20-25, 1983.

Elizabeth A Behrens, Paul Sylvester, Gina Graziano, and Abraham Clearfield, "Evaluation of A Sodium NonAtitanate, Sodium Titanosilicate, and Pharmacosiderite-Type Ion Exchangers For Strontium Removal From Doe Waste and Hanford N-Springs Groundwater Simulants", Science and Technology for Disposal of Radioactive Tank Wastes, N J Lombardo, Plenium Press, new York, 1998 pp. 287-299.

K E Thomas, J W Barnes, "Large- Scale Isolation of Sr-82 for Generator Production", 1984, pp. 123-134 Radionuclide Generators, American Chemical Society.

LANLProcedure MRDP-PSR82Rb-93, "Isolation and Purification of $^{82}$Sr from Irradiated Rb Metal Targets", Mar. 18, 1998.

LANL Procedure MRDP-PSR82-05, Isolation and Purfication of $^{82}$Sr in Sulfate Media after $U_2O_2$ Dissolution of Molybdenium Targets, Rev 8, Jun. 10, 1997.

Elizabeth A Behrens, Paul Sylvester and Abraham Clearfield, "Asement of a Sodium Nonatitante and Pharmacosiderite-Type Ion Exchangers for Strontium and Cessium Removal from DOE Waste Simulants", Environ Sci. Technol, 1998, 32, pp. 101-107.

Paul Sylsvester, Elizabeth A Behrens, Gina M Graziano, and Abraham Clearfield, "An assessment of Inorganic Ion-Exchange Materials for the Removal of Strontium from Simulated Hanford Tank Wastes", Separation Science and Technology, 34 (10), pp. 1981-1992, ©1999.

Elizabeth A Behrens, Damodara M Poojary, and Abraham Clearfield, "Syntheses, Crystal Structures, and Ion-Exchange Properties of Porous Titanosilicates, $HM_3Ti_4O_4(SiO_4)_3 4H_2O$ $(M=H^+K^+Cs^+)$, Structural Analogues of the Mineral Pharmacosiderite", Chem. Mater, 1998, 8, pp. 1236-1244.

J Letho, A. Clearfield, "The Ion Exchange of Strontium on Sodium Titante $^{Na}4^{Ti}9^O20^{xH}2^{0}$", J Radioanal, Nucl. Chem. Letters 118 / 1/1 1-13/1987.

(Continued)

*Primary Examiner*—Steven Bos
(74) *Attorney, Agent, or Firm*—Jeffrey L. Streets; Streets & Steele

(57) ABSTRACT

Sodium nonatitanate compositions, a method using the composition for recovery of $^{82}$Sr from irradiated targets, and a method using the composition for generating $^{82}$Rb. The sodium nonatitanate materials of the invention are highly selective at separating strontium from solutions derived from the dissolution of irradiated target materials, thus reducing target processing times. The compositions also have a very low affinity for rubidium, making it an ideal material for use as a $^{82}$Rb generator. Sodium nonatitanate materials of this type both improve the recovery of $^{82}$Sr and provide a safer, more effective $^{82}$Rb generator system.

66 Claims, 5 Drawing Sheets

OTHER PUBLICATIONS

T Jones, Pergamon Journals Ltd, Introduction: "Clinical Uses of 82Sr/82Rb Generators";vol. 38, 171-173, 1987.

International Patent-WO 94/19277, International Publication Date Sep. 1, 1994.

A Clearfield (ED.), "Inorganic Ion Exchange Materials", CRC Press, Boca Rotan, Florida (1982).

Paul Sylvester and Abraham Clearfield, Solvent Extraction and Ion Exchange, 16, (6), pp. 1527-1539 (1998), "The Removal of Strontium and Cesium From Simulated Hanford Groundwater Using Inorganic Ion Exchange Materials".

Gopal B. Saha, Raymundo T. Go, William J. Macintyre, Thomas H. Marwick, Annette Beachler, Janet L. King and Donald R. Neumann; "Use of the $^{82}$Sr/$^{82}$Rb Generator in Clinical PET Studies"; Nucl. Med. Biol. vol. 17. No. 8. pp. 763-768, 1990.

International Search Report, Application No. PCT/US 02/41676, International Filing Date Dec. 30, 2002, 4 sheets.

\* cited by examiner

US 7,476,377 B2

RUBIDIUM-82 GENERATOR BASED ON SODIUM NONATITANATE SUPPORT, AND IMPROVED SEPARATION METHODS FOR THE RECOVERY OF STRONTIUM-82 FROM IRRADIATED TARGETS

This application is a continuation-in-part of U.S. patent application Ser. No. 09/922,353, filed Aug. 2, 2001, now U.S. Pat. No. 6,908,598.

BACKGROUND OF THE INVENTION

1. Field of the Invention

This invention relates to the selective separation of strontium-82 from other radioisotopes, such as those resulting from irradiated molybdenum or rubidium targets, and in the manufacture of a rubidium-82 generator.

2. Background of the Related Art

The use of radioisotopes as diagnostic and imaging agents in medicine has expanded rapidly in recent years. Positron ($\beta+$) emitters are particularly useful in the study of metabolic processes because the positron-electron annihilation reaction produces a pair of gamma rays with an energy level of 511 keV travelling in opposite directions. By placing a series of detectors around a patient who has been administered a positron emitter, both the location and amount of radioactivity can be accurately determined. This property is utilized in Positron Emission Tomography (PET) to image metabolic processes in vivo. Rubidium-82 ($^{82}$Rb) is a short-lived positron-emitting isotope ($T_{1/2}$=76 seconds) that is increasingly being used to study blood flow through the heart and brain. Physiologically, rubidium is an analogue of potassium, and consequently enters the body's large potassium pool, which has a comparatively slow turnover. Thus, after $^{82}$Rb is injected intravenously, the tracer's uptake in tissue reflects the rate of delivery, i.e., blood flow, and thus $^{82}$Rb rapidly builds up in the heart. This can be used, for example, to study blood-brain barrier leakage and heart muscle perfusion.

The short half-life of $^{82}$Rb means that it must be supplied to physicians in the form of a generator, where the parent $^{82}$Sr ($T_{1/2}$=25 days) is immobilized on a solid substrate or support and $^{82}$Rb eluted as required. The generators that are currently available use hydrous tin oxide to immobilize the $^{82}$Sr and allow the elution of $^{82}$Rb by saline or other appropriate eluant. The $^{82}$Sr ($T_{1/2}$=25 days) is accompanied by unwanted $^{85}$Sr ($T_{1/2}$=64 days), generated as a by-product during the manufacture of $^{82}$Sr, wherein both isotopes have a relatively long half-life and a high radiotoxicity due to their tendency to accumulate in bone. Thus, it is essential to minimize or eliminate the introduction of $^{82}$Sr and $^{85}$Sr into a patient during the administration of $^{82}$Rb. Although hydrous tin oxide has proved acceptable to date for use in generators, new materials exhibiting far higher strontium affinities, improved strontium/rubidium separation factors and greater radiolytic stability are needed in order to lower the amount of $^{82}$Sr and $^{85}$Sr released during elution of the $^{82}$Rb.

The parent $^{82}$Sr is generated by the proton irradiation of rubidium, rubidium chloride or molybdenum targets followed by dissolution and processing to isolate the $^{82}$Sr. The demand for $^{82}$Rb generators has grown so great that there is a need to reduce processing times and to increase the yield of $^{82}$Sr from processed targets. One method of improving the supply of $^{82}$Sr is to improve the processes used to extract $^{82}$Sr from irradiated targets. Current methods utilize organic ion exchange or chelating resins to extract very low levels of strontium from dissolved targets containing molar concentrations of inert ions. However, a satisfactory separation of $^{82}$Sr from the target materials and other radioisotopes generated during the irradiation procedure requires multiple treatment steps due to the relatively low affinity and low selectivity of the organic ion exchange resins for $^{82}$Sr.

$^{82}$Sr is produced by the proton irradiation of molybdenum metal, rubidium metal and rubidium chloride targets. The irradiation process also produces a range of other radioactive isotopes (e.g., $^{88}$Y, $^{88}$Zr, $^{85}$Sr) and as a consequence, a series of carefully designed separation procedures have been designed to separate the desired $^{82}$Sr from other radioisotopes and inactive species present. The primary method used to separate $^{82}$Sr is by a series of ion exchange and selective elution steps. Typically, AG 50 W-X8 ion exchange resin is used to separate $^{82}$Sr from dissolved targets. However, this resin is relatively non-selective and will absorb numerous polyvalent cations (e.g., $^{88}$Y) in addition to the desired $^{82}$Sr. Consequently, multiple separation steps are required to isolate $^{82}$Sr from the other isotopes present.

$^{82}$Rb can be conveniently supplied to physicians in the form of a generator in which the parent $^{82}$Sr is immobilized on an ion exchange material and the $^{82}$Rb eluted when required. This means that $^{82}$Rb PET can be performed at clinical facilities where a typical generator lasts about a month before the yield of $^{82}$Rb diminishes below a usable level.

To be suitable for use in a $^{82}$Rb generator, an ion exchange material must exhibit a high affinity for strontium but a low affinity for rubidium, allowing the $^{82}$Rb daughter to be eluted from a column containing immobilized $^{82}$Sr. Generators have been proposed that were based on a number of separation media including CHELEX 100 chelating agent, $Al_2O_3$, Sb(V) hexacyanofenate, polyantimonic acid, titanium vanadate and hydrated tin(IV) oxide, with the hydrated tin(IV) oxide being the most widely used.

However, the crucial component of any system is the actual ion exchange material containing the immobilized $^{82}$Sr parent. Current systems using hydrous tin oxide have a limited life due to the breakdown of the hydrous tin dioxide, necessitating frequent replacement.

Therefore, there is a need for a highly strontium selective ion exchange material for use in place of ion exchange resins and hydrated tin(IV) oxide, so that the separation and recovery of $^{82}$Sr from Rb, RbCl and Mo targets is greatly facilitated. A replacement for the ion exchange resin will lead to a reduction in processing steps, a decrease in target processing times and thus a decrease in the cost of the $^{82}$Sr product. An ion exchange material suitable for use as a $^{82}$Rb generator will have a very high selectivity for $^{82}$Sr and a very low selectivity for $^{82}$Rb to allow elution of the $^{82}$Rb by isotonic saline or other solutions and will offer a longer operating life or improved operating conditions compared to hydrated tin(IV) oxide.

SUMMARY OF THE INVENTION

The present invention provides a method of chemically isolating strontium-82 from proton-irradiated molybdenum targets. This comprises dissolving the molybdenum metal target containing the strontium-82, adjusting the pH of the dissolved molybdenum target solution to an alkaline pH, removing precipitates from the solution, and then absorbing the strontium-82 from the solution onto a support comprising sodium nonatitanate. Sodium nonatitanate can also be applied to the efficient recovery of strontium-82 from alkaline RbCl solutions produced during the processing of proton-irradiated rubidium metal and rubidium chloride targets.

The present invention also provides a rubidium-82 generator, comprising a strontium-82 support medium comprising sodium nonatitanate. Preferably, the sodium nonatitanate is characterized by a strontium selectivity greater than 250,000 mL/g at an alkaline pH, and/or the sodium nonatitanate is characterized by a rubidium selectivity less than 100 mL/g at an alkaline pH. More preferably, the sodium nonatitanate is characterized by a strontium/rubidium separation factor greater than 1,000, and even more preferably greater than 100,000.

The rubidium-82 generator is prepared by a process comprising: preparing sodium nonatitanate from titanium isopropoxide and aqueous sodium hydroxide; heating the sodium nonatitanate at a temperature between 100° C. and 250° C. for a period between 12 hours and 2 weeks; and absorbing strontium-82 on the sodium nonatitanate from an aqueous solution comprising strontium-82 and a soluble sodium salt, wherein the sodium salt concentration is between 0.1 and 1 molar. It is also preferred that the titanium isopropoxide and the aqueous sodium hydroxide solution are provided at a sodium hydroxide to titanium isopropoxide molar ratio of greater than 0.44, but preferably providing a large molar excess of sodium hydroxide. The sodium hydroxide to titanium isopropoxide molar ratio is preferably between 1 and 10, more preferably between 2 and 6, and most preferably about 4.

Furthermore, the invention provides a process for preparing a solution containing rubidium-82. The process comprises providing a solution containing strontium-82 at a pH between 10 and 14, absorbing the strontium-82 from the solution onto a sodium nonatitanate support medium, and eluting rubidium-82 from the sodium nonatitanate support medium with a solvent. The solvent is preferably selected from the group consisting of water and saline solutions. More particularly, the solvent may be an aqueous solution having a sodium chloride concentration between 0.001 molar and 1 molar, preferably between 0.1 molar and 1 molar. The solvent may also be a pharmaceutical grade isotonic saline and buffer solution.

DETAILED DESCRIPTION OF THE INVENTION

Figure 1:
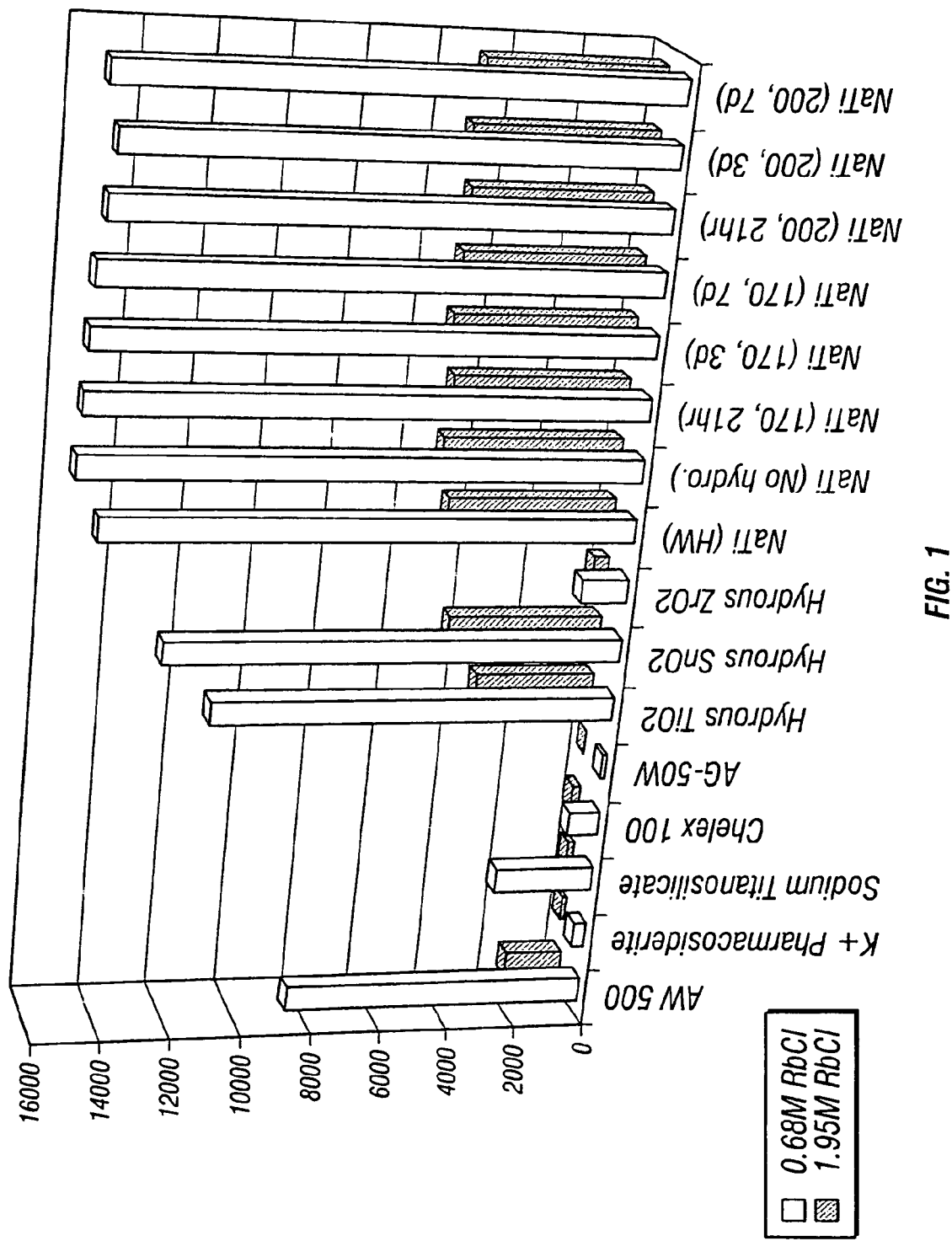
FIG. 1 is a graph showing $^{82}Sr$ $K_d$ values for the ion exchange materials from simulated rubidium and rubidium chloride target solutions.

The present invention provides improved sodium nonatitanate compositions, a method using the composition for recovery of $^{82}Sr$ from irradiated targets, and a method using the composition for generating $^{82}Rb$. The sodium nonatitanate materials of the invention are far more selective at separating strontium from solutions derived from the dissolution of irradiated target materials than current ion exchange resins used in the production of $^{82}Sr$. The present invention reduces the number of processing steps required, and thus leads to a decrease in target processing times and a reduction in the cost of the $^{82}Sr$ product. Waste generation and disposal are also decreased.

According to the present invention, synthetic conditions are adjusted to produce a material with improved properties more applicable to $^{82}Sr$ processing. The sodium nonatitanate of the present invention has been found to have a very low affinity for rubidium in addition to an exceptionally high affinity for strontium, making it ideal for use as a replacement for the hydrous tin dioxide used in current $^{82}Rb$ generators. Sodium nonatitanate materials of this type will both improve the retention of $^{82}Sr$ and lead to a safer, more effective $^{82}Rb$ generator system for clinical applications.

Sodium nonatitanate, $Na_4Ti_9O_{20}xH_2O$, is an inorganic ion exchange material that has been used for the removal of $^{90}Sr$ from neutral and alkaline nuclear wastes. The sodium nonatitanate of the present invention has a number of advantages over conventional organic ion exchange resins (e.g., CHELEX 100 chelating agent) that include: very high selectivity for trace levels of strontium in the presence of molar concentrations of other ions at alkaline PH; very low affinity for rubidium; excellent radiation, chemical and thermal stability so that there is no release of contaminants (e.g., Ti) into the $^{82}Rb$ product; rapid reaction kinetics; high cation exchange capacity; absorbed ions are readily stripped by treatment with dilute mineral acid allowing the sodium nonatitanate to be recycled, if desired; scale up of similar synthesis has already been demonstrated; and the sodium nonatitanate powder can be manufactured into pellets appropriate for column operations. Other chemically related sodium titanate materials suitable for use in the same manner as the aforementioned sodium nonatitanate ($Na_4Ti_9O_{20}xH_2O$) include other titanate materials exhibiting high Sr affinity and low Rb affinity, including Sr-Treat (available from Selion Oy) and monosodium titanate (available from Boulder Scientific) It is also anticipated that analogous zirconates may exhibit similar properties.

The invention also provides important improvements in the processing of irradiated targets to recover $^{82}Sr$. Sodium nonatitanate has a much greater affinity for $^{82}Sr$ than currently used ion exchange resins, and a low affinity for other radioactive isotopes. Consequently, the use of sodium nonatitanate greatly simplifies the extraction process by reducing the number of separation steps that are required to produce chemically pure $^{82}Sr$. Thus, targets can be processed more rapidly and the recovery of $^{82}Sr$ improved. Improved isotope selectivity may also facilitate the isolation of other useful isotopes from the targets, leading to greater payback from target processing operations.

Furthermore, less than 1 g of sodium nonatitanate material is needed in a $^{82}Rb$ generator and 1 kg of this material is expected to be sufficient to process a large number of targets, even if the sodium nonatitanate material is not recycled and is disposed of after one use. Consequently, the additional cost incurred by the use of sodium nonatitanate will be negligible in comparison with the cost savings achieved in the $^{82}Sr$ production.

It has been determined that replacing hydrous tin dioxide with sodium nonatitanate reduces the amount of $^{82}Sr$ released during the operation of the $^{82}Rb$ generator, thereby reducing the exposure of the patient to $^{82}Sr$. Sodium nonatitanate is also more chemically stable and less likely to leach non-radioactive contaminants into solution during operation of the generator. The sodium nonatitanate is also more amenable to recycling since the $^{82}Sr$ can readily be stripped with mineral acid without producing additional impurities. Recycling of $^{82}Sr$ generators is already being used as a source of additional $^{82}$Sr, and improvements to the recycling procedure (obtained by using a superior ion exchange material) will facilitate the recovery of $^{82}$Sr from this source.

Although the sodium nonatitanate may be used as a direct replacement for hydrous tin dioxide in the $^{82}$Rb generator, it is also possible to use sodium nonatitanate in the form of a disposable add-on filter that could be used to trap any $^{82}$Sr that is leached from the generator during the production of $^{82}$Rb.

The first step in preparing a $^{82}$Rb generator is to load the parent $^{82}$Sr onto the sodium nonatitanate material and place the ion exchange material into a suitable column. It is essential that sufficient time be allowed for the $^{82}$Sr to be absorbed by the sodium nonatitanate material in order to maximize the loading of the parent radioisotope per gram of ion exchange material.

For an $^{82}$Rb generator, the sodium nonatitanate may be loaded into the column and then loaded with $^{82}$Sr although this method results in depositing a disproportionate amount of the $^{82}$Sr at the top of the column with the remainder of the column remaining as a guard bed to collect any $^{82}$Sr that migrates down the column. Alternatively, the sodium nonatitanate may be loaded with $^{82}$Sr before being placed in an ion exchange column to avoid preferentially loading the $^{82}$Sr on the top of the ion exchange. A high concentration of radioactivity on a very small volume of sodium nonatitanate may result in undesirable radiolytic problems. Although sodium nonatitanate has been shown to be highly resistant to radiation damage, it is always considered prudent to avoid any unnecessary radiation exposure.

In the medical field, use of the $^{82}$Rb generator preferably provides a saline solution that can be intravenously injected into a patient as an imaging agent at a pH of between about 4.5 and about 7. To achieve the desired pH range of the eluted $^{82}$Rb solution, a neutralization step may be performed on the sodium nonatitanate to lower the pH of the sodium nonatitanate. An $^{82}$Rb generator having sodium nonatitanate that has not been neutralized to a lower pH produces an $^{82}$Rb eluate solution having a higher pH than is desired for an injectable pharmaceutical in the medical field. For example, using a normal saline eluant having an initial pH of about 7.6 to elute $^{82}$Rb from an $^{82}$Rb generator having sodium nonatitanate that has not been neutralized to a lower pH can produce an eluate with a pH as high as 9.5. Even though over time the pH of the eluate slowly declines as more eluant is run through the generator, it is preferable and more efficient that the $^{82}$Rb eluate produced from the generator is immediately suitable for medical use. In one experiment, it was determined that a 2.92 g alkaline nonatitanate column required about 44 L of pH 6.2 saline eluant throughput to lower the pH level of the eluate to within the desired pH range. However, the use of such a high volume of eluant before the $^{82}$Rb solution is produced at a desired pH level is unacceptable.

The neutralization step added to the nonatitanate synthesis effectively lowers the pH of the ion exchanger and provides an $^{82}$Rb solution having the desired pH range from the first use of the generator. The neutralization step includes adding an acid to the final stage of the nonatitanate synthesis. This neutralization step has no significant effect on the high separation factor that the nonatitanate possesses for strontium and rubidium as required for use in an $^{82}$Rb generator. However, using the sodium nonatitanate that has been neutralized to a lower pH results in an $^{82}$Rb product having an acceptable pH difference of less than one pH unit between the eluant and the eluate.

The neutralization step includes resuspending the sodium nonatitanate product in a liquid and then adding an acid to lower the pH to between about 7 and about 9, preferably between about 7.2 and about 8.5. The pH is more preferably lowered to between about 7.5 and about 8.3 and most preferably to between about 7.8 and about 8.2. Sodium nonatitanate is partially neutralized by contacting the sodium nonatitanate product with the acidic liquid. The product may be centrifuged, the supernatant poured off, and, if desired, the process repeated to neutralize the sodium nonatitanate product again to obtain the target pH. The liquid may be any suitable liquid such as normal saline, dilute sodium chloride, water or preferably, deionized water. Any strong acid may be added to lower the pH such as, for example, nitric acid, sulfuric acid, or preferably hydrochloric acid.

It is important to maintain the pH of the sodium nonatitanate above a minimum pH during the neutralization step because lowering the pH below neutral also lowers the separation efficiency of Sr/Rb. There is a correlation shown in between pH and the uptake of both $^{85}$Sr and $^{82}$Rb. At high pH, the uptake of $^{85}$Sr is high while the uptake of $^{82}$Rb is low. At pH between about 6 and about 7, the uptake of $^{85}$Sr starts to decrease while the uptake of $^{82}$Rb remains the same or slightly increases. At pH values lower than about 4, the affinity for $^{85}$Sr decreases dramatically.

As the pH of the equilibrium saline solution passing through the column increases, the nonatitanate affinity for the strontium increases while the affinity for the rubidium decreases. Therefore, lowering the pH of the produced nonatitanate by performing a neutralizing step at the end of the method of producing the nonatitanate results in generator having a shorter life. To optimize the life time and separation efficiency, either the neutralization step may be omitted or a less complete neutralization step may be performed to achieve a lesser degree of neutralization.

Optionally, an adjustment may be made to the pH of the eluate product obtained from the nonatitanate column that was produced without a neutralization step or was only slightly neutralized during the neutralization step. If the eluate product from the generator has a pH above the desired range, the pH of the eluate product may be decreased to the desired pH range by adding an acid. Acceptable acids include any acid suitable for neutralizing the eluent without rendering the neutralized eluent unsuitable for injection into a patient during a medical procedure as known by those having ordinary skill in the art. Suitable acids would include, for example, hydrochloric acid (HCl) and acetic acid ($CH_3COOH$). HCl is preferred because the salt produced by the neutralizing reaction is NaCl, which is already present in the solution.

The acid may be added automatically to adjust the pH or the acid may be added manually. A pH meter preferably measures the pH of the eluate product. Alternatively, other means, such as pH indicating strips, may be used to measure the pH of the eluate. Preferably a pH meter monitors the pH of the eluate as the acid is added to obtain the eluate target pH of between about 4.5 and about 7. The acid may be added using a gravity system to drip or pour the acid into the eluate. Alternatively, a pressure system, such as a syringe, a pump or a gas pressurized system may be used to add the acid to the eluate. When the acid is added automatically, a controller monitors the output signal from a pH meter and adjusts a valve or a pump rate to add the amount of acid necessary to obtain the eluate target pH. If adjusted manually, acid may be added to the eluate by an operator, preferably in pre-packaged amounts, until a pH meter or indicator strip indicates that the target pH has been achieved. Preferably, the acid is added automatically to the eluate as the eluate flows from the column.

The size of the sodium nonatitanate particles used in the generator is an important factor. The use of large particles of sodium nonatitanate in a column provides low flow resistance of the eluant through the column but large particles cannot be packed into a column or elutable container as densely as smaller particles may be packed. Furthermore, large particles create long diffusion paths over which the $^{82}$Rb generated by the decay of $^{82}$Sr atoms located deep in the particle must travel while diffusing from the centers of the large particles. In contrast, fine particles of sodium nonatitanate permit more material to be packed into a column of a given volume and provide shorter diffusion paths out of the particles, but the fine particles produce greater flow resistance to the eluant during the elution of the $^{82}$Rb from the generator.

Therefore, the $^{82}$Rb generator preferably includes smaller particles of sodium nonatitanate because the shorter diffusion path allows the particles to equilibrate with the eluant more quickly and because the smaller particles pack more densely into a column of a given size. Both of these factors together promote the elution of $^{82}$Rb using a small volume of saline solution as the eluant and obtaining a high concentration of $^{82}$Rb in the eluate. Preferably, the particles of sodium nonatitanate are made as small as possible without causing excessive back pressure from the flow of the eluant through the column. Preferably, the size of the particles used in the $^{82}$Rb generator range between about 50 μm and about 200 μm. More preferably, the particle size of the sodium nonatitanate is between about 75 and about 150 μm and most preferably between about 75 and about 100 μm.

Low porosity is a preferred characteristic of the sodium nonatitanate particles for use in the $^{82}$Rb generator of the present invention. If the particles are highly porous, much of the parent $^{82}$Sr deposits within the pores, which creates a longer diffusion path for the $^{82}$Rb to diffuse from the pores into the saline eluant. The $^{82}$Rb generated from the $^{82}$Sr deposited deep within a pore continues to decay while diffusing from the pore into the eluant stream, which results in a loss of the generated $^{82}$Rb and thereby, a lower $^{82}$Rb yield.

The column aspect ratio is a factor that contributes to the optimum operation of the $^{82}$Rb generator of the present invention. The aspect ratio of a column is the column length over the column diameter. Increasing column length at constant diameter provides for greater retention of $^{82}$Sr and thereby minimizes the amount of leached $^{82}$Sr in the final eluate product. However, as the column length increases, total pressure drop through the column increases, causing higher back pressure at the inlet to the column. The column aspect ratio affects the properties of the $^{82}$Rb generator even at constant column volume and sodium nonatitanate mass.

A long, narrow column having a high aspect ratio offers greater resistance to the flow of the eluant and generates a higher backpressure at the inlet to the column. Because the velocity of a given volume of eluant is higher in a column having a high aspect ratio, the flow through the column having a high aspect ratio is more turbulent, which increases mixing within the eluant stream. Comparatively, a short, wide column having a low aspect ratio operates with a lower velocity of a given volume of eluant through the column and operates at lower pressure drop with less mixing. However, channeling through the bed can occur at low velocities resulting in the eluant bypassing some of the ion exchange material and providing a lower yield. While a wide range of column aspect ratios are acceptable, preferably, without limitation, the aspect ratio may be between about 4 and 50, more preferably between about 6 and about 20.

Preferably, the column or other elutable container is not loaded with uniform material over its entire length. The portion of the column closest to the generator outlet preferably holds sodium nonatitanate containing no $^{82}$Sr, serving as a guard bed to intercept any $^{82}$Sr or $^{85}$Sr released from the generator. By intercepting and capturing any released $^{82}$Sr and $^{85}$Sr, the product eluant is safe for use as an $^{82}$Rb tracer. The guard bed may be formed with sodium nonatitanate that was produced without the neutralization step so that the affinity to capture strontium is at its highest level and the affinity to capture rubidium is at its lowest level. Optionally, the guard bed may be placed in a second separate container, receiving the eluate from the outlet of the generator, to filter any strontium from the eluant eluted from the $^{82}$Rb generator. Alternatively, a guard bed may be installed in the generator as described above coupled with a separate filter containing sodium nonatitanate as an added precaution.

Optionally, the sodium nonatitanate may be supported on the surface of a non-porous support. Placing the sodium nonatitanate in a thin layer on a non-porous support provides the advantage of placing all of the sodium nonatitanate in close contact with the eluant, thereby minimizing the length of the diffusion path of the $^{82}$Rb from the nonatitanate to the eluant. Suitable non-porous support materials include inorganic materials that are not damaged in a high radiation field, such as fiberglass, fine glass beads, ceramics, and other similar materials known to those skilled in the art. It is critical that any material chosen for this function does not release anything into the eluate that could contaminate the product.

The examples that follow disclose the methods and materials for the $^{82}$Rb generator. Examples 12-18 further disclose the nonatitanate neutralized to a lower pH for providing an eluate having a pH within the desired range.

EXAMPLES

These Examples investigated the suitability of sodium nonatitanate for the use in separating $^{82}$Sr from irradiated targets and in the construction of an $^{82}$Sr/$^{82}$Rb generator. Initial batch experiments compared the rubidium and strontium selectivities of a number of different sodium nonatitanate samples with commercially available ion exchange materials (e.g., AW 500, CHELEX 100 chelating agent) and some experimental materials that had also exhibited high strontium selectivities (e.g., sodium titanosilicate). Column experiments were then performed using target simulants and generator simulants on materials that exhibited favorable selectivity characteristics. Some work was also performed to investigate the likely interference from other isotopes present in irradiated targets on the production of $^{82}$Sr.

Example 1

Preparation of Sodium Nonatitanate

Sodium nonatitanate (NaTi) was synthesized hydrothermally as follows. 77.5 g of titanium isopropoxide was added to 84.35 g of a 50 wt % solution of NaOH with vigorous stirring and 60 mL of deionized water was added. The resultant gel was heated at approximately 108° C. for 3 hours, transferred to a hydrothermal pressure vessel with an additional 90 mL of deionized water, and heated at either 170° C. or 200° C. for times ranging from 21 hours to 1 week. After the allotted time, the materials were filtered, washed with ethanol to remove residual base and dried at 60° C. The mass of sodium nonatitanate produced was approximately 31 g.

Each sample was characterized using x-ray powder diffraction (XRD). The reaction is outlined in Equation 1.

$$9\ Ti(OC_3H_7)_4 + 4\ NaOH(aq) \rightarrow Na_4Ti_9O_{20} \cdot xH_2O + 9\ C_3H_7OH \quad (1)$$

The crystallinity of the material was shown to be dependent upon the reaction time and temperature, with the most crystalline materials being produced after 1 week of hydrothermal treatment (200° C. for 7 days). Samples that received no hydrothermal treatment, or only a few days, were virtually amorphous with only a few very broad reflections visible on the XRD pattern.

The theoretical cation exchange capacity (CEC) of sodium nonatitanate is quite high and has a value of 4.74 meq/g, which compares favorably with organic ion exchange resins.

Alternative titanium salts that could be used to manufacture sodium nonatitanate include titanium tetrachloride, $TiCl_4$, and titanium sulfate, $TiOSO_4 \cdot xH_2SO_4 \cdot yH_2O$. However, hydrolysis of these salts leads to the generation of hydrochloric acid and sulfuric acid, respectively, and thus additional base is required to neutralize the acids during the hydrothermal process. The final product also needed to be exhaustively washed to remove residual sodium chloride or sodium sulfate. Consequently, titanium isopropoxide (which hydrolyzes to form propanol) or titanium dioxide $TiO_2$ is the preferred starting material because the final product is free from additional sodium salts.

Example 2

Determination of Strontium Selectivity

Sodium nonatitanate and a variety of other ion exchange materials were obtained and evaluated for use in the separation of $^{82}Sr$ from targets and in a $^{82}Rb$ generator. These materials are described below in Table 1.

TABLE 1

Characteristics of Ion Exchange Materials Evaluated in this Study

| Material | Source | Sample Preparation |
|---|---|---|
| Na-Clinoptilolite | GSA Resources, AZ | Ground to powder. |
| AW500 | Aldrich (1.6 mm Pellets) | Ground to powder |
| Hydrous $SnO_2$ | Synthesized in house | NaOH + $SnCl_4$. Washed with acetic acid/sodium acetate buffer |
| K+ Pharmacosiderite ($K_3H(TiO)_4(SiO_4)_3 \cdot 4H_2O$) | Synthesized according to literature method | None. Used as synthesized |
| Sodium Titanosilicate ($Na_2Ti_2O_3SiO_4 \cdot 2H_2O$) | Synthesized according to literature method | None. Used as synthesized |
| AG 50W-X8 (Na+) (25-50 Mesh) | BioRad. Strong acid ion exchange resin. | Converted to Na+ form (for alkaline solutions only) |
| CHELEX 100 (Na+) (50-100 Mesh) | BioRad. Chelating resin with iminodiacetic acid functionality | None. Used as received |
| Sodium Nonatitanate | Honeywell, IL | None. Used as received |
| Hydrous $SiO_2$ | Synthesized in house | Acetic acid hydrolysis of tetraethyl orthosilicate. Washed with $H_2O$ |

TABLE 1-continued

Characteristics of Ion Exchange Materials Evaluated in this Study

| Material | Source | Sample Preparation |
|---|---|---|
| Hydrous $TiO_2$ | Synthesized in house | Hydrolysis of titanium isopropoxide. Washed with $H_2O$ |
| Hydrous $ZrO_2$ | Synthesized in house | $ZrOCl_2$ + NaOH. Washed with deionized water |

The strontium selectivity of the ion exchange materials of Table 1 was evaluated in sodium chloride and rubidium chloride solutions using radiotracer techniques. Samples were evaluated using a simple batch technique to allow the rapid screening of a large number of materials over a range of ionic strengths. Blanks were run for each matrix to check for any loss of strontium during filtration or absorption of strontium onto the scintillation vials. In all solutions evaluated, strontium absorption was negligible.

0.05 g of each of the ion exchange materials was contacted with 10 mL of a solution, spiked with $^{89}Sr$, in a capped scintillation vial. (The total strontium content was approximately 1.6 ppm, thus preventing any loss of strontium in solution due to precipitation of sparingly soluble $Sr(OH)_2$ at alkaline pH values.) The mixtures were shaken for 6 hours, filtered through a 0.2 μm syringe filter and the residual activity determined using liquid scintillation counting (LSC). Distribution Coefficients ($K_d$ values) were then determined according to Equation 2:

$$K_d = (A_i - A_f)/A_f * V/m \quad (2)$$

where: $A_i$=initial activity in solution (counts per minute (cpm)/mL)
$A_f$=final activity in solution (cpm/mL)
V=volume of solution (mL)
m=mass of exchanger (g)

The final pH of the solution was also noted. The period of 6 hours was chosen to allow equilibrium to be reached for each of the ion exchange materials. However, previous work on the titanosilicates and titanates had shown the reaction rates to be rapid with the majority of the uptake occurring in only a few minutes. The concentration of the chloride solutions was varied from 1 M to 0.001 M to evaluate the effect of increasing $Rb^+$ and $Na^+$ concentrations on the uptake of $Sr^{2+}$. All experiments were performed in duplicate, and if significant variations between duplicate samples occurred, the experiments were repeated until good agreements on the $K_d$ values were obtained. The results are shown in Tables 2 and 3 and represented the average $K_d$ obtained, quoted to 3 significant figures.

TABLE 2

Strontium Selectivity Data from Unbuffered Sodium Chloride Solutions

| Ion Exchange Material | $K_d$ mL/g 1M NaCl | 0.1M NaCl | 0.01M NaCl | 0.001M NaCl |
|---|---|---|---|---|
| Na-Clinoptilolite | 8 | 124 | 3,260 | 36,900 |
| AW500 | 1,860 | 88,300 | 1,270,000 | 1,210,000 |
| Hydrous $SnO_2$ | 767 | 43,000 | 124,000 | 51,800 |
| K+ Pharmacosiderite | 18,300 | 251,000 | 594,000 | 281,000 |
| Sodium Titanosilicate | 556,000 | 273,000 | 119,000 | 42,900 |
| AG 50W (Na+) | 32 | 3,380 | 365,000 | 2,510,000 |
| CHELEX 100 (Na+) | 610 | 26,400 | 726,000 | 1,300,000 |

TABLE 2-continued

Strontium Selectivity Data from Unbuffered Sodium Chloride Solutions

| Ion Exchange Material | $K_d$ mL/g 1M NaCl | 0.1M NaCl | 0.01M NaCl | 0.001M NaCl |
|---|---|---|---|---|
| NaTi (Honeywell) | 80,600 | 1,030,000 | 258,000 | 166,000 |
| NaTi (No hydrothermal) | 1,530,000 | 2,570,000 | 739,000 | 372,000 |
| NaTi (170° C., 21 hr) | 1,030,000 | 1,240,000 | 272,000 | 172,000 |
| NaTi (170° C., 3 d) | 959,000 | 633,000 | 218,000 | 93,100 |
| NaTi (170° C., 7 d) | 167,000 | 834,000 | 264,000 | 90,400 |
| NaTi (200° C., 21 hr) | 439,000 | 1,390,000 | 197,000 | 120,000 |
| NaTi (200° C., 3 d) | 261,000 | 898,000 | 251,000 | 158,000 |
| NaTi (200° C., 7 d) | 195,000 | 955,000 | 265,000 | 214,000 |
| $ZrO_2$ | 3,360 | 52,200 | 213,000 | 232,000 |

TABLE 3

Strontium Selectivity Data from Unbuffered Rubidium Chloride Solutions

| Material | $K_d$ mL/g 1M RbCl | 0.1M RbCl | 0.01M RbCl | 0.001M RbCl |
|---|---|---|---|---|
| Na-Clinoptilolite | 19 | 3 | 88 | 11,000 |
| AW500 | 9,750 | 107,000 | 1,020,000 | 1,280,000 |
| Hydrous $SnO_2$ | 766 | 66,100 | 104,000 | 51,800 |
| K+ Pharmacosiderite | 1,950 | 40,800 | 419,000 | 427,000 |
| Sodium Titanosilicate | 12,600 | 94,700 | 164,000 | 179,000 |
| AG-50W (Na+) | 44 | 3,870 | 237,000 | 800,000 |
| CHELEX 100 (Na+) | 1,580 | 38,400 | 555,000 | 977,000 |
| NaTi (Honeywell) | 13,900 | 108,000 | 279,000 | 324,000 |
| NaTi (No hydrothermal) | 14,220 | 116,000 | 345,000 | 429,000 |
| NaTi (170° C., 21 hr) | 10,500 | 71,700 | 193,000 | 205,000 |
| NaTi (170° C., 3 d) | 15,100 | 39,500 | 68,000 | 95,200 |
| NaTi (170° C., 7 d) | 23,000 | 55,800 | 31,200 | 110,000 |
| NaTi (200° C., 21 hr) | 11,000 | 66,400 | 110,000 | 103,000 |
| NaTi (200° C., 3 d) | 10,600 | 56,800 | 146,000 | 158,000 |
| NaTi (200° C., 7 d) | 10,500 | 57,400 | 146,000 | 158,000 |
| $ZrO_2$ | 3,000 | 42,400 | 184,000 | 221,000 |

Comparing the selectivity data from sodium and rubidium solutions, it is evident that rubidium ions cause a reduction in affinity for the strontium ion for all of the exchangers indicating that the affinity of these materials for rubidium is significantly higher than the affinity for sodium ions. The pH of the final solutions was generally alkaline for the nonatitanates (NaTi) and titanosilicates, with pH values as high as 12 being measured. This was due to hydrolysis of the exchangers resulting in the absorption of protons and the release of sodium ions, thus increasing the pH of the aqueous phase. This effect can be overcome, if desired, by buffering the solution.

The most distinct trend was observed in 1M NaCl solutions for the sodium nonatitanate samples. The highest $K_d$ was observed for the non-hydrothermal material and the $K_d$ values decreased with increasing reaction time for both the 200° C. and 170° C. materials. Clearly, strontium uptake is facilitated by having a low-crystallinity material. This suggests that as the crystallinity increases and the size of the nonatitanate crystallites also increases, it becomes thermodynamically less favorable for exchange of the sodium ions by strontium. It is also interesting to note that the majority of the sodium nonatitanates exhibit a higher selectivity for strontium in 1M NaCl than in 0.001M NaCl. This indicates that the higher ionic strength facilitates the $Na^+/Sr^{2+}$ exchange reaction and more than compensates for the increased competition for the ion exchange sites from the additional $Na^+$ ions.

This data shows that sodium nonatitanate is an ideal material for the recovery of $^{82}Sr$ from irradiated rubidium and rubidium chloride targets and in the manufacture of a $^{82}Rb$ generator.

Example 3

Rubidium Selectivity from NaCl Solutions

For an ion exchange material to be suitable for use in a 82Rb generator, it must have a very high selectivity for strontium to prevent any loss of $^{82}Sr$ from the ion exchange column and release to the patient undergoing a PET scan. This property was clearly demonstrated in Example 2. It must also have a very low selectivity towards rubidium, thus allowing $^{82}Rb$ to be released into solution as saline is passed through the $^{82}Rb$ generator. Consequently, the rubidium selectivity of the ion exchange materials was evaluated in sodium chloride media following the procedure described in Example 2. The same procedure was followed using $^{86}Rb$ to spike the solutions to give an activity of approximately 200,000 cpm/mL. Total rubidium in solution was <0.05 ppm. The distribution coefficients of the materials are shown below in Table 4.

TABLE 4

Rubidium Selectivity Data from Unbuffered Sodium Chloride Solutions

| Ion Exchange Material | 1M NaCl | 0.1M NaCl | 0.01M NaCl | 0.001M NaCl |
|---|---|---|---|---|
| AW500 | 116 | 620 | 4920 | 21900 |
| Hydrous $SnO_2$ | 1 | 6 | 36 | 290 |
| K+ Pharmacosiderite | 148 | 475 | 2030 | 4020 |
| Sodium Titanosilicate | 8,010 | 194,000 | 114000 | 75800 |
| AG 50W (Na+) | 7 | 75 | 688 | 6680 |
| CHELEX 100 (Na+) | 3 | 8 | 43 | 256 |
| NaTi (Honeywell) | 9 | 102 | 488 | 817 |
| NaTi (No hydrothermal) | 4 | 59 | 280 | 446 |
| NaTi (170° C., 21 hr) | 9 | 56 | 209 | 297 |
| NaTi (170° C., 3 d) | 7 | 46 | 198 | 311 |
| NaTi (170° C., 7 d) | 3 | 15 | 47 | 71 |
| NaTi (200° C., 21 hr) | 8 | 79 | 334 | 502 |
| NaTi (200° C., 3 d) | 8 | 52 | 207 | 307 |
| NaTi (200° C., 7 d) | 4 | 25 | 111 | 178 |
| $ZrO_2$ | 1 | 12 | 60 | 154 |

TABLE 4A

Strontium-Rubidium Separation Factor

| Ion Exchange Material | 1M NaCl | 0.1M NaCl | 0.01M NaCl | 0.001M NaCl |
|---|---|---|---|---|
| AW500 | 16.0 | 142 | 258 | 55.3 |
| Hydrous SnO2 | 767 | 7,167 | 3,444 | 179 |
| K+ Pharmacosiderite | 124 | 528 | 293 | 69.9 |
| Sodium Titanosilicate | 69.4 | 1.41 | 1.04 | 0.57 |
| AG 50W (Na+) | 4.57 | 45.1 | 531 | 376 |
| CHELEX 100 (Na+) | 203 | 3,300 | 16,884 | 5,078 |
| NaTi (Honeywell) | 8,956 | 10,098 | 529 | 203 |
| NaTi (No hydrothermal) | 382,500 | 43,559 | 2,639 | 834 |
| NaTi (170 C., 21 hr) | 114,444 | 22,143 | 1,301 | 579 |
| NaTi (170 C., 3 d) | 137,000 | 1,370 | 1,101 | 299 |
| NaTi (170 C., 7 d) | 55,667 | 55,600 | 5,617 | 1,273 |
| NaTi (200 C., 21 hr) | 54,875 | 17,595 | 590 | 239 |
| NaTi (200 C., 3 d) | 32,625 | 17,269 | 1,213 | 515 |
| NaTi (200 C., 7 d) | 48,750 | 38,200 | 2,387 | 1,202 |
| ZrO2 | 3,360 | 4,350 | 3,550 | 1,506 |

TABLE 4B

Percent Rubidium Retention Generated on 0.1 g of Exchanger in NaCl Solution

| Ion Exchange Material | 1M NaCl | 0.1M NaCl | 0.01M NaCl | 0.001M NaCl |
|---|---|---|---|---|
| AW500 | 18.8 | 55.4 | 90.8 | 97.8 |
| Hydrous SnO2 | 0.2 | 1.2 | 6.7 | 36.7 |
| K+ Pharmacosiderite | 22.8 | 48.7 | 80.2 | 88.9 |
| Sodium Titanosilicate | 94.1 | 99.7 | 99.6 | 99.3 |
| AG 50W (Na+) | 1.4 | 13.0 | 57.9 | 93.0 |
| CHELEX 100 (Na+) | 0.6 | 1.6 | 7.9 | 33.9 |
| NaTi (Honeywell) | 1.8 | 16.9 | 49.4 | 62.0 |
| NaTi (No hydrothermal) | 0.8 | 10.6 | 35.9 | 47.1 |
| NaTi (170 C., 21 hr) | 1.8 | 10.1 | 29.5 | 37.3 |
| NaTi (170 C., 3 d) | 1.4 | 8.4 | 28.4 | 38.3 |
| NaTi (170 C., 7 d) | 0.6 | 2.9 | 8.6 | 12.4 |
| NaTi (200 C., 21 hr) | 1.6 | 13.6 | 40.0 | 50.1 |
| NaTi (200 C., 3 d) | 1.6 | 9.4 | 29.3 | 38.0 |
| NaTi (200 C., 7 d) | 0.8 | 4.8 | 18.2 | 26.3 |
| ZrO2 | 0.2 | 2.3 | 10.7 | 23.5 |

From the data in Table 4, it is clear that the all of the sodium nonatitanate materials have a very low affinity for rubidium, particularly in the presence of relatively high amounts of sodium ions. In general, the rubidium selectivity decreased with increasing reaction time for both series of nonatitanates (170° C. and 200° C.) with the lowest affinity being demonstrated by the sample that was heated hydrothermally at 170° C. for 1 week. Uptake was negligible in 1M NaCl and the very low reduction in activity that was noted could be accounted for by absorption of rubidium during filtration and by pipetting errors during the counting procedure. Consequently, samples with $K_d$ values that were below 10 mL/g can be considered to have no affinity at all for $^{86}$Rb. Some rubidium uptake was evident in very dilute sodium solutions, but the $K_d$ values were low for all of the titanate samples. This suggests that the uptake of rubidium was more likely due to the materials having an exceptionally low affinity for sodium rather than any real affinity for rubidium. All of the sodium nonatitanate materials performed better than the commercially available sample obtained from Honeywell, Inc. The materials are clearly ideal for use in a $^{82}$Rb generator.

Hydrous tin dioxide exhibited some of the lowest rubidium affinities and was comparable with CHELEX 100 chelating agent, the best of the nonatitanates and the hydrous zirconium dioxide. However, hydrous tin dioxide exhibited much lower strontium $K_d$ values than the nonatitanates. Therefore, nonatitanate materials are preferred because they have higher strontium/rubidium separation factors. Hydrous tin dioxide also has a limited pH stability range and significant dissolution and release of absorbed strontium is likely to occur should any significant pH perturbations occur outside the range of pH 4 to pH 9. Radiation stability of hydrous tin dioxide is also limited, with particle breakdown causing current $^{82}$Rb generators to be replaced before decay has reduced the $^{82}$Rb below useable levels.

The rubidium selectivity data also indicates that AW500, potassium Pharmacosiderite and the sodium titanosilicate have a strong affinity for rubidium in a range of saline solutions. Consequently, these materials will be unsuitable for use in a 82Rb generator and have only limited applications in the processing of irradiated target materials.

Example 4

Strontium and Rubidium Selectivity in 0.1M Sodium Acetate/Acetic Acid Buffer

In order to prevent hydrolysis reactions from raising the pH as described above, some strontium and rubidium selectivity experiments were performed in a 0.1M sodium acetate/acetic acid buffer solution. In these tests, the final pH remained between 5.2 and 6.3, which is a more clinically acceptable pH for an $^{82}$Rb infusion. Rubidium $K_d$ values remained low, as expected, following the trend observed in Table 5. Strontium $K_d$ values were considerably lower, with a maximum $K_d$ value of 80,000 mL/g being obtained for the sodium nonatitanate sample that was heated hydrothermally at 170° C. for 21 hours. This is considerably lower than the $K_d$ value of over 1,200,000 mL/g that was obtained in unbuffered 0.1M NaCl (pH~12). The $K_d$ values obtained for the other ion exchange materials were also considerably lower. However, the Sr/Rb separation factors remained high and the sodium nonatitanates still outperformed hydrous tin dioxide and the organic ion exchange resins. The affinity of sodium nonatitanate for strontium is greatest at higher pH values.

Example 5

Molybdenum Targets

The basic steps of a proposed process to obtain $^{82}$Sr from irradiated molybdenum targets are as follows:
1. Dissolve the irradiated molybdenum target in 30% hydrogen peroxide, ensuring excess hydrogen peroxide is destroyed.
2. Add sodium hydroxide to bring the pH to approximately 12.
3. Filter the solution to remove any precipitate. It is predicted that the majority of $^{88}$Zr and $^{59}$Fe will be found in the precipitate, and experiments have confirmed that 99% or more of the $^{88}$y precipitated out of solution on the addition of NaOH.
4. Pass the solution through a column of sodium nonatitanate and wash the column with two bed volumes of 0.1M NaCl, adjusted to pH 12 with NaOH. $^{82}$Sr and $^{85}$Sr will be absorbed. $^{82}$Rb and other Rb isotopes will remain in the aqueous phase. Molybdate anions will also pass through the column.
5. The column can then be stripped using dilute mineral acid to recover the $^{82}$Sr and the sodium nonatitanate reused or discarded.

There is a range of other isotopes present in addition to $^{82}$Sr, including $^{75}$Se, $^{73}$As, $^{74}$As, $^{7}$Be, $^{68}$Ge, $^{48}$V, $^{60}$Co (and other Co isotopes), $^{54}$Mn, $^{51}$Cr and $^{95m}$Tc. In the alkaline target solution, Se, As, V, Ge, Cr, Mn and Tc are expected to be present as anions and thus will not be absorbed onto the sodium nonatitanate. Significant amounts of Co would be expected to precipitate when the target solution is neutralized, and thus little is expected to be available under alkaline conditions to absorb onto the sodium nonatitanate. The most likely isotope to be absorbed is beryllium, because it is a Group II metal with a similar aqueous chemistry to strontium. However, the affinity of sodium nonatitanate for Group II metals decreases in the order Sr>Ca>Mg. No data is available for beryllium, but if the trend continues, the affinity would be expected to be low. Thus, any absorbed $^7$Be would be readily removed by an alkaline sodium chloride (or similar) wash.

The current process for recovering $^{82}$Sr from irradiated rubidium metal and rubidium chloride targets requires minimal modification to facilitate the use of sodium nonatitanate. Both targets are processed following standard processing procedures to generate rubidium chloride solutions in an ammonia/ammonium chloride buffer solution. These solutions are then passed through a sodium nonatitanate column and washed with additional buffer to remove any weakly held rubidium cations. Strontium and possibly some other cationic species present will be absorbed onto the nonatitanate column, whereas rubidium cations, ammonium cations and anions will rapidly pass through the column. If additional cations are absorbed onto the sodium nonatitanate, they can be selectively removed by washing with an appropriate eluant (e.g., citrate, nitrilotriacetate.) The strontium selectivity of sodium nonatitanate has been shown to be unaffected by a number of common complexants and as a consequence, it should be a relatively simple manner to elute any undesirable cations from the column, leaving pure $^{82/85}$Sr.

FIG. 1 clearly shows the exceptionally high affinity of the sodium nonatitanate materials in comparison with the currently utilized organic resin CHELEX 100 chelating agent. All of the sodium nonatitanates performed equally well in the buffered rubidium target solutions indicating that the synthetic conditions are not too important when the material is being used in solutions containing high concentrations of rubidium ions. Thus, by replacing the CHELEX 100 chelating agent with sodium nonatitanate, a more efficient 82Sr isolation can be achieved.

It has also been shown that it is possible to tailor the selectivity of the sodium nonatitanate to achieve the optimum Sr/Rb separation by manipulating the reaction conditions. The differing selectivities were most obvious in sodium solutions, with the less crystalline materials exhibiting the highest strontium distribution coefficients. However, the series of nonatitanates showed little difference in behavior when the predominant cation in solution was Rb$^+$. The materials synthesized clearly demonstrated superior characteristics to the commercially available sample in almost all matrices evaluated. The majority of the sodium nonatitanate samples also exhibited greater strontium selectivities than hydrous tin dioxide in a range of sodium chloride solutions, from 1M to 0.001M. Rubidium selectivities were low, making the sodium nonatitanate ideal as a replacement for hydrous tin dioxide in a $^{82}$Rb generator.

Commercially, one method of $^{82}$Sr production is via the proton spallation reaction with natural molybdenum metal targets. A simulated molybdate target solution was prepared as follows: 12.5 g of molybdenum powder was carefully dissolved in 30% $H_2O_2$ solution and made up to a total volume of 500 mL to produce a clear yellow solution of molybdic acid, $H_2MoO_4$. Solid sodium hydroxide granules totaling 10.9 g were then carefully added to neutralize the solution and bring the pH to approximately 12.3. The colorless solution was then filtered to remove any precipitate. This alkaline molybdate solution was spiked with either $^{86}$Rb or $^{89}$Sr and $K_d$ values determined as described previously. Separation factors for the strontium/rubidium selectivity were also calculated by dividing the strontium $K_d$ by the rubidium $K_d$, thus allowing the relative affinities of the ion exchange materials to be directly compared. The results are illustrated below in Table 5.

TABLE 5

Strontium and Rubidium Absorption from Simulated Molybdate Target Solutions

| Material | Sr Kd, mL/g | Rb Kd, mL/g | Separation Factor |
| --- | --- | --- | --- |
| AW500 | 7,070 | 194 | 36.4 |
| K+ Pharmacosiderite | 187,000 | 142 | 1320 |
| Sodium Titanosilicate | 547,000 | 6500 | 84.2 |
| CHELEX 100 (Na+) | 3,120 | 5 | 624 |
| AG 50W-X8 (Na+) | 69 | 18 | 3.83 |
| NaTi (Honeywell) | 337,000 | 27 | 12,500 |
| NaTi (No hydrothermal) | 1,690,000 | 12 | 141,000 |
| NaTi (170° C., 21 hr) | 1,000,000 | 12 | 83,300 |
| NaTi (170° C., 3 d) | 829,000 | 14 | 59,200 |
| NaTi (170° C., 7 d) | 324,000 | 3 | 108,000 |
| NaTi (200° C., 21 hr) | 954,000 | 12 | 79,500 |
| NaTi (200° C., 3 d) | 687,000 | 11 | 62,500 |
| NaTi (200° C., 7 d) | 772,000 | 9 | 85,800 |
| ZrO$_2$ | 168,000 | 8 | 21,000 |

From this data, it is clear that the sodium nonatitanate materials are far superior to CHELEX 100 chelating agent and AG 50W-X8 ion exchange resins for the recovery of $^{82}$Sr from irradiated molybdenum targets. High $K_d$ values in excess of 500,000 mL/g indicate that almost 100% strontium removal was achieved by some of the nonatitanate samples, with the residual strontium in solution approaching background levels. In the alkaline conditions used in this test, the CHELEX 100 chelating agent resin had the lowest affinity for strontium of all of the materials evaluated. The selectivity of the sodium nonatitanate for rubidium was lowest for the sodium nonatitanate material that was prepared by heating for 1 week at 170° C. to obtain a relatively crystalline product. However, strontium selectivity also decreased with increasing reaction time.

The best overall strontium/rubidium separation factor was obtained for the material that had not undergone any hydrothermal treatment. All of the materials performed better than the commercially available nonatitanate materials. Thus, it is possible to alter the selectivity of the material by controlling the reaction conditions to produce an improved sodium nonatitanate material for use in $^{82}$Sr separations. Rubidium selectivities were very low for all of the nonatitanates, indicating minimal rubidium absorption would occur in a column process and that any rubidium absorbed would be readily removed by a dilute saline wash.

The sodium titanosilicate, potassium Pharmacosiderite and AW500 exhibit selectivities for rubidium that are too high to allow their use in the selective removal of $^{82}$Sr from irradiated molybdenum targets. This high selectivity would result in some rubidium being retained on the column that would not be readily removed by a simple saline wash, thus leading to contamination of the $^{82}$Sr product with both radioactive and stable rubidium isotopes. Hydrous tin oxide was not evaluated because, due to the amphoteric nature of tin, significant dissolution would be expected at a pH in excess of 12.

Example 6

Acid Molybdate Target Solutions

Sodium nonatitanate has a relatively low affinity for strontium at pH values less than 6, and was not expected to exhibit any affinity for strontium from the acidic molybdate target solutions prior to the addition of sodium hydroxide. $K_d$ values were determined to confirm this and to compare it with the $K_d$ values for both CHELEX 100 chelating agent and AG 50W-X8 under identical conditions. The data obtained is shown below in Table 6.

TABLE 6

Affinity of Selected Ion Exchange Materials for Strontium in Acidic Molybdate Target Solutions

| Ion Exchange Material | Sr $K_d$ mL/g | Final pH of Solution |
|---|---|---|
| CHELEX 100 | 25 | 1.43 |
| AG 50W-X8 | 18,300 | 1.42 |
| Sodium Nonatitanate (Honeywell) | 1,260 | 1.53 |

These data clearly indicate that for the processing of acid molybdate solutions, the strong acid ion exchange resin AG 50W-X8 is the preferred medium. However, the Sr $K_d$ value of 18,300 mL/g in the acidic media is nearly two orders of magnitude lower than the $K_d$ value of 1,690,000 mL/g that was obtained for the best of the sodium nonatitanate materials in alkaline molybdate solutions. Consequently, it is evident that $^{82}$Sr can be recovered more effectively from alkaline solution using sodium nonatitanate than is currently achieved using AG 50W-X8 from acidic media.

Example 7

Rubidium and Rubidium Chloride Target Solutions

The processing of either rubidium chloride or rubidium metal targets follows a similar procedure once the target has been successfully dissolved. In essence, $^{82}$Sr needs to be selectively extracted from a solution of RbCl in a 0.1 M NH$_3$/0.1 M NH$_4$Cl buffer adjusted to a pH of between 9 and 10. Batch experiments were performed in simulated buffer solutions to determine the strontium selectivity in the presence of high concentrations of rubidium ions. Only the ion exchange materials that exhibited high strontium selectivities in the initial scoping studies with NaCl solutions were evaluated. $K_d$ values were obtained as described previously. Two rubidium chloride solutions were selected which represent typical rubidium concentrations obtained during the processing of rubidium metal (1.95 M Rb$^+$) and rubidium chloride targets (0.68 M Rb$^+$). In both cases, CHELEX 100 chelating agent is used in the preliminary step to remove the $^{82}$Sr from the buffered rubidium solutions. The $K_d$ values for the ion exchange materials In the buffered rubidium solutions, there is little difference between the different nonatitanates evaluated. This is in stark contrast to the sodium molybdate solutions where a large variation in the performance of the titanates was observed. The nonatitanates were clearly the most effective materials at removing strontium from the buffered solutions with strontium $K_d$ values of around 15,000 mL/g in 0.68 M Rb$^+$ solutions and approximately 5,000 mL/g in 1.96 M Rb$^+$ solutions. By contrast, CHELEX 100 chelating agent ion exchange resin gave $K_d$ values of less than 1,000 mL/g in both solutions. Hydrous titanium oxide and hydrous tin oxide also exhibited appreciable $K_d$ values, but they performed less efficiently than the nonatitanates in both solutions. Consequently, this data demonstrates that using sodium nonatitanate in place of CHELEX 100 chelating agent ion exchange resin will greatly increase the amount of strontium extracted from the target solutions.

The ion exchange materials were also evaluated for their rubidium selectivity from 0.1 M NH$_3$/0.1M NH$_4$Cl buffer solution. The buffer was prepared, spiked with $^{86}$Rb and the pH adjusted to approximately. 9.25 with concentrated ammonia. $^{86}$Rb $K_d$ values were then determined following the method described earlier. All of the sodium nonatitanates had a $K_d$<20 mL/g. The very low rubidium selectivity in the pure buffer is almost certainly due to competition from NH$_4^+$ ions for the available ion exchange sites. Consequently, absorption of rubidium during the processing of rubidium and rubidium chloride targets will be minimal, and any rubidium absorbed will be readily removed by washing with additional 0.1 M NH$_3$/0.1M NH$_4$Cl buffer solution. Thus, a clean separation of $^{82}$Sr from these targets can be obtained using sodium nonatitanate.

The performance could also be improved by removing the buffer and increasing the pH to improve the amounts of strontium absorbed. (Buffers were initially utilized to maximize the performance of the organic ion exchange resins currently used and are not essential to the $^{82}$Sr recovery process.)

Example 8

Kinetic Experiments

In order for the sodium nonatitanate materials to find applications in the processing of irradiated target solutions, they must exhibit fast ion exchange kinetics allowing solutions to be passed through an ion exchange column at an acceptable rate. The kinetics of strontium absorption from alkaline molybdate target solutions was evaluated using a simple batch procedure. Ion exchange material, in the amount of 0.05 g, was shaken with 10 mL of molybdate solution spiked with $^{89}$Sr to give a total activity of approximately 155,000 cpm/mL. After an allotted time, the material was filtered through a 0.2 m syringe filter and the activity in the aqueous phase determined by LSC. The results are shown below in FIG. 2.

Figure 2:
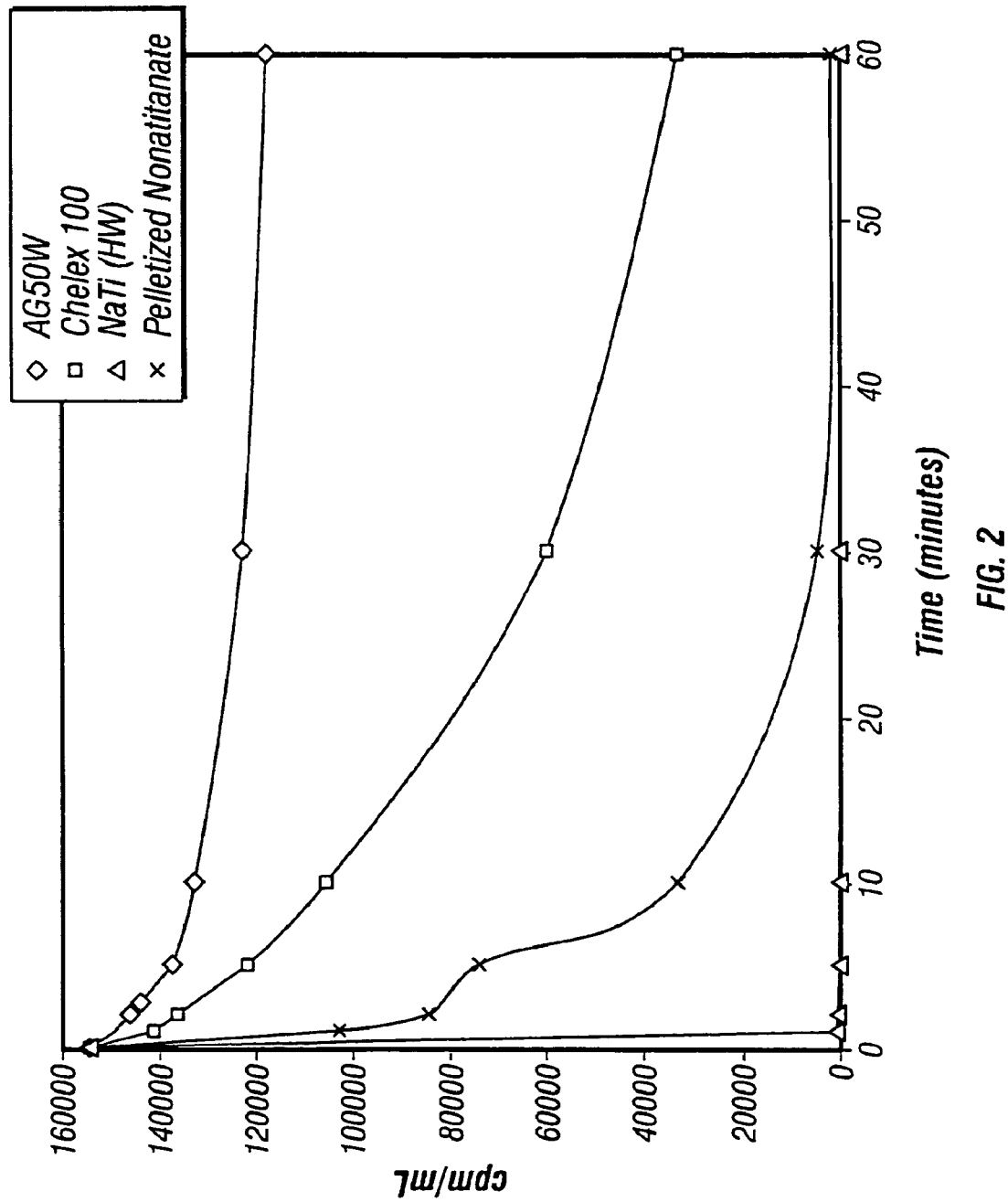
FIG. 2 is a graph showing the reduction of $^{82}Sr$ activity with increasing time.
Figure 3:
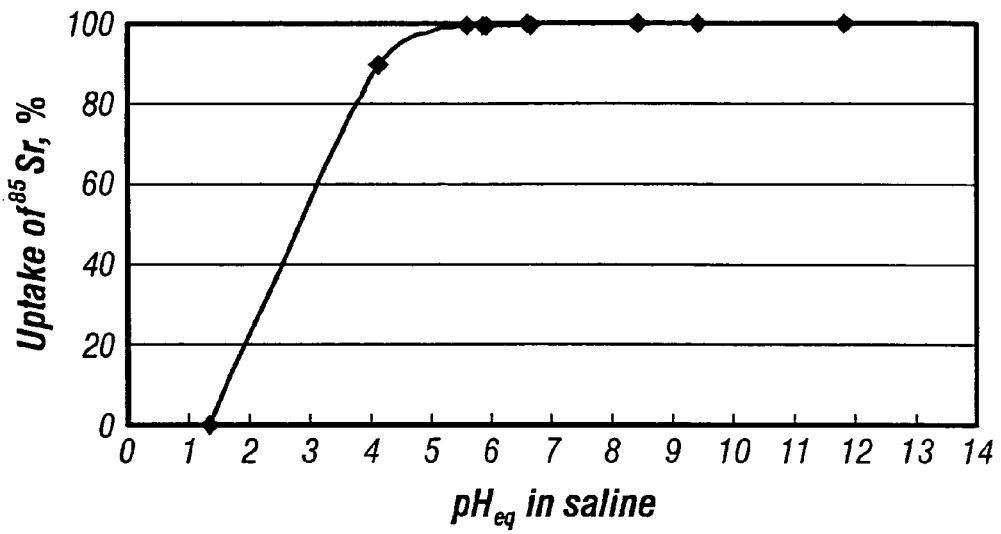
FIG. 3 is a graph showing the effect of pH on the uptake of $^{85}Sr$ using normal saline as an eluant.

From the data in FIG. 2, it is clear that the reaction kinetics for the sodium nonatitanate powder is extremely rapid, with over 99% of the $^{89}$Sr removed in only 1 minute. By contrast, the reaction kinetics of the organic ion exchange resins was much slower and the total amount of $^{89}$Sr removed after 1 hour was much less.

The exceedingly rapid kinetics can partly be explained by the fact that the nonatitanate was in the form of a fine powder, whereas the two resins were in the form of beads (see Table 1). As a consequence, a relatively slow reaction rate would be expected for the beads because the uptake of $^{82}$Sr will be dependent upon the rate of diffusion of the $^{82}$Sr to the internal exchange sites. The rate of uptake of a sample of sodium nonatitanate pellets (using hydrous titanium dioxide as a binder) was significantly slower than the powdered form, but the kinetics and amount of $^{82}$Sr absorbed was still significantly better than for either of the two organic resins. As the pelletization process is improved, it is expected that the kinetics and selectivity of the pelletized sodium nonatitanate will improve substantially. Other sodium nonatitanate powders of varying crystallinities also showed rapid kinetics. Other potentially suitable binders for forming suitable pellets include titanium isopropoxide or tetraethyl orthosilicate (TEOS) as a binder precursor.

Example 9

$^{82}$Sr Removal from Irradiated Targets Using Pelletized Sodium Nonatitanate

A sample of sodium nonatitanate was mixed with titanium isopropoxide as a binder and the resulting paste dried at 105° C. for 12 hours. The material was gently broken up using a mortar and pestle and then sieved to produce particles in the range 40 to 60 mesh. The binder content was approximately 20%. These particles were then used to assess the extraction of $^{89}Sr$ from simulated target solutions.

1 mL of pelletized sodium nonatitanate was slurried into a column and the target simulant that had been spiked with $^{89}Sr$ to give an activity of approximately 200,000 cpm/mL was passed through the column at a flow rate of 15 mL per hour. The amount of activity removed from solution was then determined. The results are given below in Table 7.

TABLE 7

Removal of $^{89}Sr$ from Irradiated Target Solutions

| Target | Solution Composition | Volume (mL) | $^{89}Sr$ Removed (%) |
|---|---|---|---|
| Rubidium Metal | 1.95M RbCl in 0.1M $NH_3/NH_4Cl$ Buffer, pH 10 | 20 | 97.3 |
| Rubidium Chloride | 0.68M RbCl in 0.1M $NH_3/NH_4Cl$ Buffer, pH 10 | 28 | 98.8 |
| Molybdenum Metal | 0.26M $Na_2MoO_4$, pH 12 | 20 | 99.9 |

This data clearly shows the effectiveness of sodium nonatitanate for removing strontium isotopes from $^{82}Sr$ target materials. Rubidium absorption under these conditions is minimal.

Example 10

Elution of Strontium

Strontium was quantitatively eluted from the sodium nonatitanate column of Example 9 using 6M nitric acid. Hydrochloric acid was found to be much less effective and also resulted in breakdown of the sodium nonatitanate particles and blocked the ion exchange column.

Example 11

Formation of Acid Washed Sodium Nonatitanate Pellets

As described in Example 1, sodium nonatitanate (NaTi) was synthesized hydrothermally as follows. 77.5 g of titanium isopropoxide was added to 84.35 g of a 50 wt. % solution of NaOH with vigorous stirring and 60 mL of deionized water was added. The resultant gel was heated at approximately 108° C. for 3 hours, transferred to a hydrothermal pressure vessel with an additional 90 mL of deionized water, and heated at either 170° C. or 200° C. for times ranging from 21 hours to 1 week.

After the hydrothermal treatment disclosed in Example 1, the vessel was cooled down and the sodium nonatitanate was transferred into a centrifuge tube and separated from solution by centrifugation (3,300 rpm for 14 minutes). The recovered nonatitanate was washed by resuspending it in 500 mL of deionized water (DIW) by mixing it thoroughly and then again separated by centrifugation. These washing steps were repeated twice.

The pH of deionized water was adjusted to 3 by the addition of HCl. The washed nonatitanate was added to the low pH DIW and mixed thoroughly. The nonatitanate was recovered through centrifugation and dried in a 60° C. oven for two nights. The hard acid washed nonatitanate was then ground, sized and sieved to 50×100 mesh and 100×200 mesh using nylon screens. Fines were washed off and the pellets were dried at 60° C.

Example 12

Formation of Neutralized Nonatitanate Pellets

Sodium nonatitanate was prepared by treating it hydrothermally for 21 hours at 200° C. The white product was washed by suspending it in DIW with stirring. 3 M nitric acid was added dropwise to maintain a pH of 8.0 for one hour. After a final DIW wash, the material was dried overnight at 60° C. The dried material was sized into particles using a series of nylon sieves, and collecting the 100×200 mesh particles for column use. The sized material was rinsed of fines.

Figure 4:
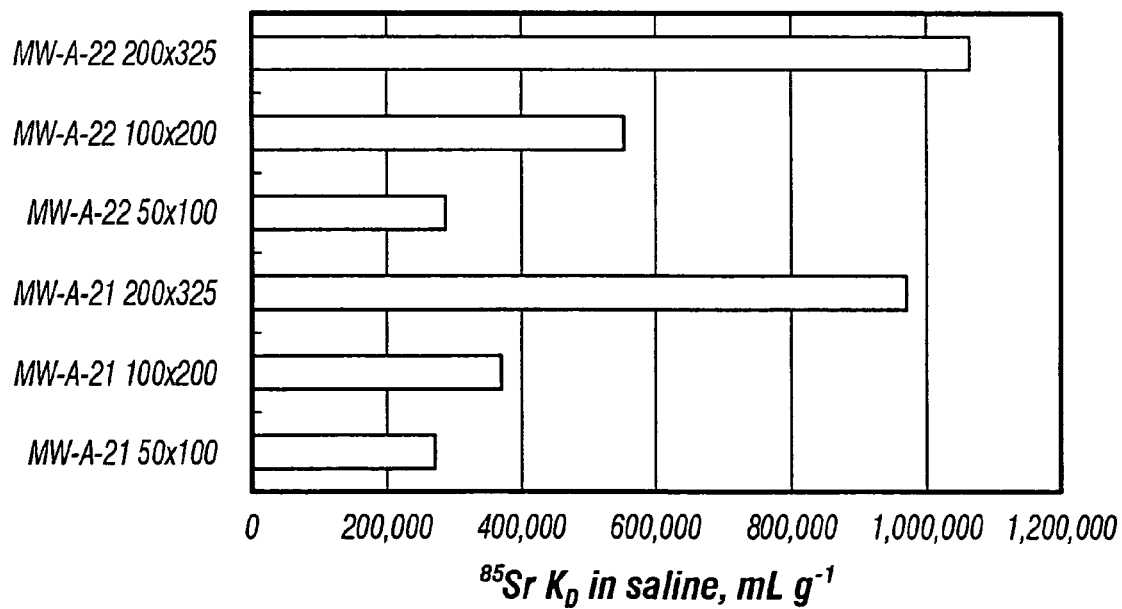
FIG. 4 is a graph showing $^{85}Sr$ $K_d$ values in normal saline for NaTi samples of various pellet size.

Pellet size is a factor that affects the performance of the 82Sr/82Rb generator column because higher Sr uptake is obtained with finer particles due to the faster sorption with the material having the smaller particle size and resulting greater surface area. FIG. 4 is a graph showing the $^{85}Sr$ $K_d$ values in normal saline for NaTi samples of various pellet size, without a binder.

Example 13

Packing Column with Sodium Nonatitanate and Loading with Parent $^{82}Sr$

To prepare the generator column, the sodium nonatitanate particles were suspended in saline and slurried into the column. First, 1.125 g of exchanger was introduced into the column and sandwiched between two filters (GB003, Schleicher & Schuell blotting paper). This bed provided a guard bed to trap any strontium that was released from the bed above. Next, about 0.375 g of exchanger was equilibrated with inactive strontium ($SrCl_2$) in saline, to simulate a full loading of $^{82}Sr$. This material was placed on top of the guard bed and topped with a third filter.

Example 14

Balancing pH by the Addition of Acid

Nonatitanate is prepared as described in Example 12 except that the pH is adjusted to 11 instead of 8.0. The material is equilibrated with $^{82}Sr$ and loaded into a column having a guard bed as described in Example 13. The column is eluted with normal (0.9%) saline with 50 mL/min flow. The resulting solution contains a high yield of $^{82}Rb$ in 49 mL of solution at pH 10. This solution is dosed with 1 mL of 0.05 M HCl, neutralizing the basicity of the saline to yield 50 mL of solution at pH 7, suitable for use as a medical pharmaceutical as previously described.

Example 15

Supported Sodium Nonatitanate

Fine glass helices of the type commonly used to pack a high efficiency distillation column are dipped in a dilute (5 wt. %) solution of sodium metasilicate. The helices are allowed to drain so only a thin film of solution remains on their surfaces. The helices are then gently rolled in finely powdered (<400 mesh, <38 μm) sodium nonatitanate to coat the surfaces with the powder. The coated helices are dried and the metasilicate solution is rendered insoluble by heating to 175° C. in air for 16 hours. The helices are now ready for use in a generator.

Example 16

Pelletization of the Ion Exchanger

After hydrothermal treatment and washing the material was then resuspended in DIW that has had the pH adjusted to 3 with HCl, mixed thoroughly after which the solid and liquid phases were separated as before. The wet exchanger was dried in a 60° C. oven for two nights, the hard product ground, sized and sieved to 50×110 mesh and 100×200 mesh using nylon screens. Fines were washed off and the pellets dried at 60° C. These pellets were ready for further testing.

Example 17

Elution at Lower pH

Figure 5:
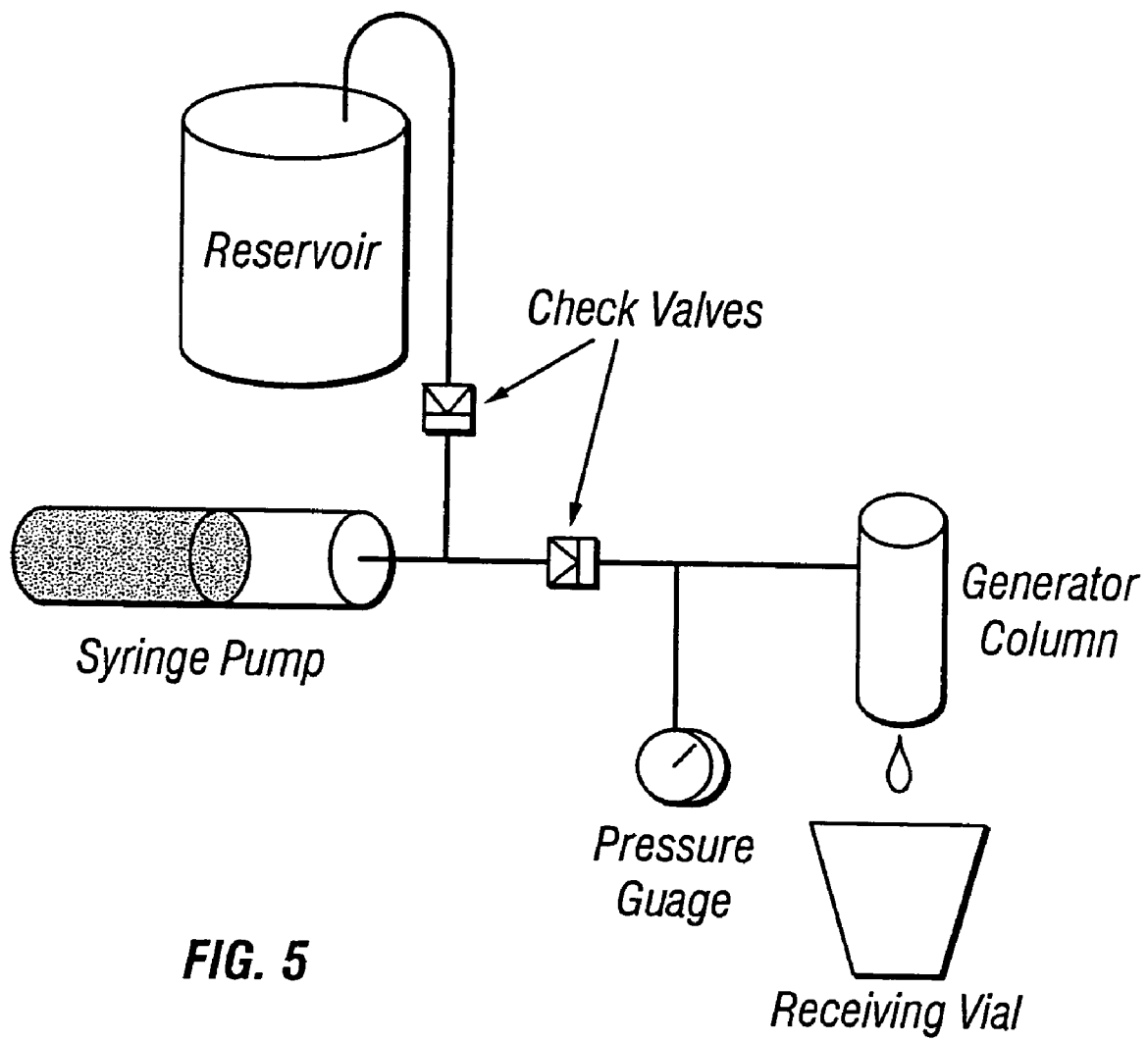
FIG. 5 is a schematic drawing of a system having a sodium nonatitanate column in accordance with the present invention.

The column packed with NaTi (neutralized to pH 8.0 as described in Example 12) was eluted using the syringe pump system as shown in FIG. 5. USP saline (purchased in 1 L bottles from Fisher Scientific), was methodically drawn into a 60 mL syringe and pushed through the column in 50 mL increments at a flow rate of 50 mL/min. The eluates were collected in 50 mL falcon tubes. A 5 mL sample of each eluate was analyzed for $^{85}$Sr activity by gamma spectroscopy (Wallac 1480 Wizard 3) and the pHs recorded. Over 20 L of USP saline were pumped through the column during the experiment with no $^{85}$Sr breakthrough observed.

Figure 6A:
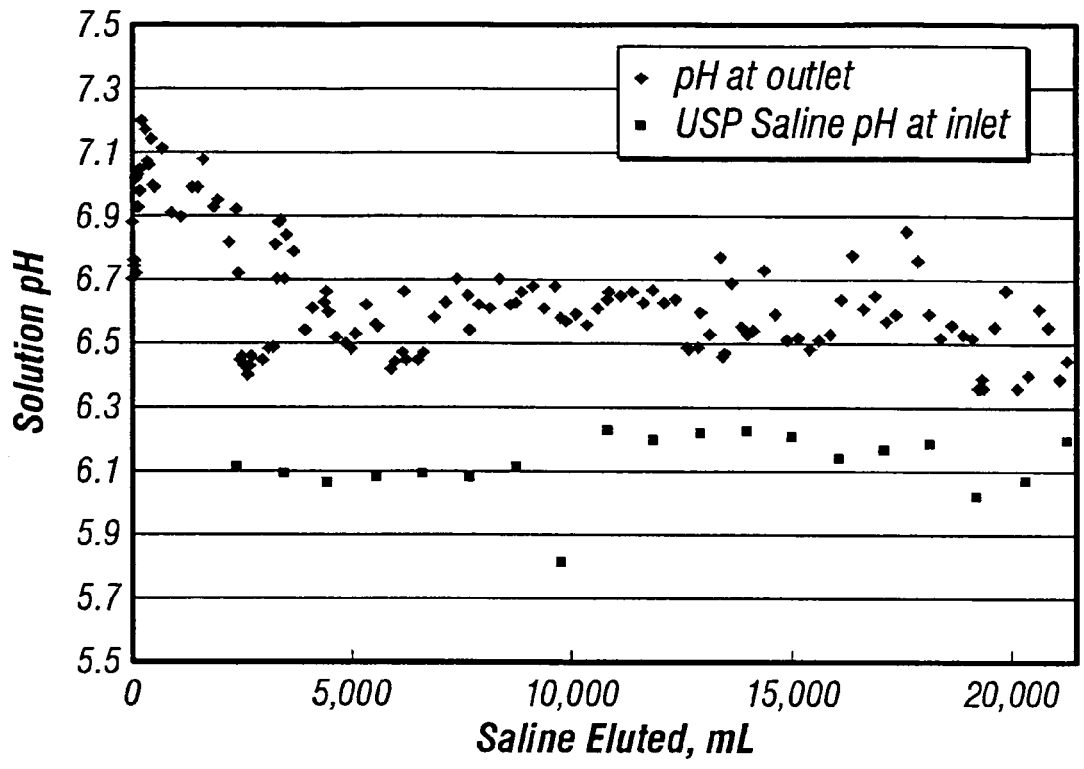
FIGS. 6A-6B are graphs showing the pH of saline solutions at the inlet and outlet of a $^{82}Sr/^{82}Rb$ column.
Figure 6B:
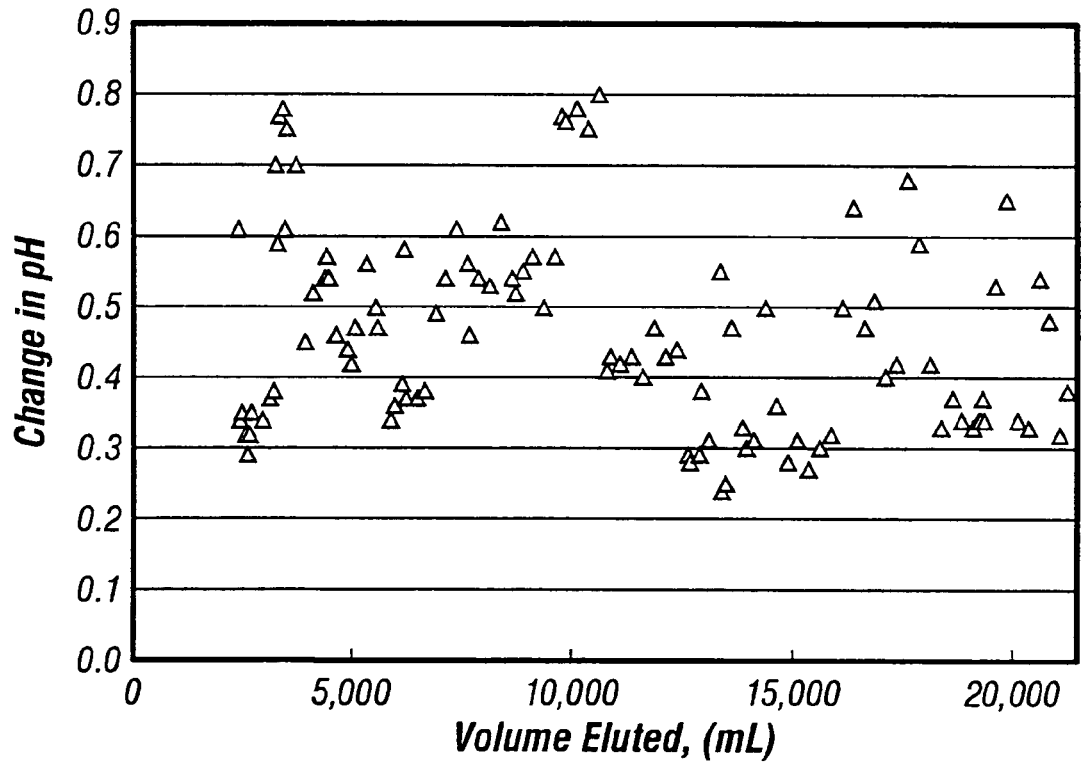

The results are shown in FIGS. 6A-6B, which show that all of the saline was eluted at pH values acceptable for injection into a human. The neutralized material retains its strong strontium binding ability and no breakthrough of $^{82,85}$Sr was observed in over 20 L of eluted USP saline (after the initial washout in 200 mL).

Table 8 provides reproducibility and quality control data of final batches of sodium nonatitanate described by the synthesis procedure, sizing of pellets and $^{85}$Sr and $^{86}$Rb $K_d$ values.

| | | | Sizing of pellets | | | | | | |
|---|---|---|---|---|---|---|---|---|---|
| ID | Treatment | Synthesis Yield (Dry weight, g) | 50-100 mesh (% of total) | 100-200 mesh (% of total) | >100 mesh (% of total) | >200 mesh (% of total) | Loss to sizing (% of total) | $^{85}$Sr Kd in saline/ equilibration pH | $^{86}$Rb Kd in saline/ equilibration pH |
| TA-A-78 | 'Acid wash' | 28.3 | 65.6 | 23.0 | x | 9.5 | 1.98 | 1,970,6325.5/9.89 | 56.6/9.89 |
| TA-A-80 | 'Acid wash' | 19.3 | 47.2 | 27.5 | x | 21.6 | 3.77 | 10,603,837.65/9.44 | 84.65/9.39 |
| TA-A-83 | 'Acid wash' | 21.4 | 48.9 | 21.0 | x | 25.7 | 4.48 | 5,866,141.8/9.43 | x |
| TA-A-84 1-12 | Neutralized (pH 8) | 12.3 | x | 46.9 | x | 53.1 | 0.00 | 520,951.3/6.82 | 188.6/6.87 |
| TA-A-84 3-19 | Neutralized (pH 8) | 13.0 | 38.4 | x | 59.7 | x | 1.85 | 1,518,239.55/6.72 | 232.75/6.79 |
| TA-A-87 3-30 | Neutralized (pH 8) | 13.2 | 60.8* | x | 34.0 | x | 5.16 | 1,120,327.3/6.72 | 232.65/6.70 |
| TA-A-87 4-1 | Neutralized (pH 8) | 12.0 | 52.9 | x | 42.2 | x | 4.88 | 1,007,944.3/6.78 | 245.3/6.78 |
| TA-A-88 | 'Acid wash' | 25.0 | 49.4 | x | 43.0 | x | 7.64 | 4,656,739.8/9.67 | 71.5/9.62 | designates materials used for Kd determination
equilibration time of several days for Kd determination While the foregoing is directed to the preferred embodiment of the present invention, other and further embodiments of the invention may be devised without departing from the basic scope thereof, and the scope thereof is determined by the claims that follow.

What is claimed is:

1. A process for preparing a rubidium-82 generator, comprising:
    preparing sodium nonatitanate from titanium isopropoxide and aqueous sodium hydroxide;
    heating the sodium nonatitanate at a temperature between 100° C. and 250° C. for a period between 12 hours and 2 weeks;
    lowering the pH of the sodium nonatitanate; and
    absorbing strontium-82 on the neutralized sodium nonatitanate from an aqueous solution comprising strontium-82 and a soluble sodium salt.

2. The method of claim 1, wherein the soluble sodium salt concentration is between about 0.1 and about 1 molar.

3. The process of claim 1, wherein the soluble sodium salt is sodium chloride.

4. The process of claim 1, wherein the molar ratio of aqueous sodium hydroxide to titanium isopropoxide is in excess of 0.44.

5. The process of claim 1, wherein the molar ratio of aqueous sodium hydroxide to titanium isopropoxide is between 2 and 6.

6. The process of claim 1, wherein the aqueous sodium hydroxide is about 50 wt % sodium hydroxide.

7. The process of claim 1, further comprising:
filtering the sodium nonatitanate from the solution.

8. The process of claim 7, further comprising:
washing the sodium nonatitanate with ethanol.

9. The process of claim 8, further comprising:
drying the sodium nonatitanate.

10. The process of claim 1, wherein the molar ratio of aqueous sodium hydroxide to titanium isopropoxide is between about 1 and 10.

11. The process of claim 1, wherein the sodium nonatitanate is heated in a pressure vessel.

12. The process of claim 1, wherein the sodium nonatitanate is prepared in the absence of titanium chlorides and sulfates.

13. The process of claim 1, wherein the step of neutralizing the sodium nonatitanate further comprises:
suspending the sodium nonatitanate in a liquid; and
adding an acid to the liquid to lower the pH.

14. The process of claim 13, wherein the step of adding an acid lowers the pH to between about 7 and about 9.

15. The process of claim 13, wherein the step of adding and acid lowers the pH to between about 7 and about 8.3.

16. The process of claim 13, wherein the liquid comprises water.

17. The process of claim 13, wherein the acid is a strong mineral acid.

18. The process of claim 1, further comprising:
loading the sodium nonatitanate into a column.

19. The process of claim 1, further comprising:
supporting the sodium nonatitanate on a non-porous substrate.

20. The process of claim 1, wherein the solution containing strontium-82 is an acidic aqueous solution.

21. A process for preparing a solution containing rubidium-82, comprising:
providing a solution containing strontium-82;
absorbing strontium-82 onto a sodium nonatitanate support medium;
eluting rubidium-82 from the sodium nonatitanate support medium with an eluant;
receiving a rubidium-82 eluate from the sodium nonatitanate support medium; and
adjusting a pH of the eluate.

22. The process of claim 21, wherein the eluant is selected from the group consisting of water and saline solutions.

23. The process of claim 21, wherein the eluant is an aqueous solution having a sodium chloride concentration between 0.001 molar and 1 molar.

24. The process of claim 21, wherein the eluant is an aqueous solution having a sodium chloride concentration between 0.2 molar and 1 molar.

25. The process of claim 21, wherein the eluant is a pharmaceutical-grade saline and buffer solution.

26. The process of claim 21, wherein the sodium nonatitanate is characterized by a strontium/rubidium separation factor greater than 12,500.

27. The process of claim 21, wherein the sodium nonatitanate is characterized by a strontium/rubidium separation factor greater than or equal to 59,200.

28. The process of claim 21, wherein the sodium nonatitanate is characterized by a strontium/rubidium separation factor greater than or equal to 100,000.

29. The process of claim 21, further comprising:
disposing the sodium nonatitanate support medium into a column.

30. The process of claim 21, wherein the eluate is alkaline.

31. The process of claim 21, further comprising:
buffering the solvent.

32. The process of claim 21, wherein the pH of the eluate is adjusted to between about 4.5 and about 7.

33. The process of claim 21, wherein the pH of the eluate is adjusted to a pH suitable for injecting into a patient during a medical procedure.

34. The process of claim 21, wherein the step of adjusting a pH of the eluate comprises;
adding an acid to the eluate.

35. The process of claim 34, wherein the acid is HCl.

36. The process of claim 21, further comprising:
partially neutralizing the sodium nonatitanate before the step of absorbing strontium-82 onto a sodium nonatitanate support medium.

37. A process for preparing a rubidium-82 generator, comprising:
preparing sodium nonatitanate from titanium tetrachloride or titanium sulfate and aqueous sodium hydroxide;
heating the sodium nonatitanate at a temperature between 100° C. and 250° C. for a period between 12 hours and 2 weeks;
lowering the pH of the sodium nonatitanate; and then
absorbing strontium-82 on the sodium nonatitanate from an aqueous solution comprising strontium-82 and a soluble sodium salt.

38. The process of claim 37, wherein the soluble sodium salt concentration is between about 0.1 and about 1 molar.

39. The process of claim 37, wherein the soluble sodium salt is sodium chloride.

40. The process of claim 37, wherein the aqueous sodium hydroxide is about 50 wt % sodium hydroxide.

41. The process of claim 37, wherein the molar ratio of aqueous sodium hydroxide to titanium tetrachloride or titanium sulfate is between about 1 and 12.

42. The process of claim 37, further comprising:
filtering to collect the sodium nonatitanate; and
washing the sodium nonatitanate to remove sodium chloride or sodium sulfate.

43. The process of claim 37, wherein lowering the pH of the sodium nonatitanate further comprises:
suspending the sodium nonatitanate in a liquid; and
adding an acid to the liquid to lower the pH.

44. The process of claim 43, wherein adding the acid lowers the pH to between about 7 and about 9.

45. The process of claim 43, wherein adding the acid lowers the pH to between about 7.2 and about 8.

46. The process of claim 43, wherein the liquid comprises water.

47. The process of claim 43, wherein the acid is a strong mineral acid.

48. The process of claim 37, further comprising:
loading the sodium nonatitanate into a column.

49. The process of claim 37, further comprising:
supporting the sodium nonatitanate on a substrate.

50. The process of claim 37, wherein the solution containing strontium-82 is an acidic aqueous solution.

51. A process, comprising:
   eluting a solution of rubidium-82 from a strontium-82 support medium comprising sodium nonatitanate with an aqueous eluant; and
   adjusting a pH of the solution.

52. The process of claim 51, wherein the aqueous eluant is selected from the group consisting of water and saline solutions.

53. The process of claim 51, wherein the aqueous eluant has a sodium chloride concentration between 0.001 molar and 1 molar.

54. The process of claim 51, wherein the aqueous eluant has a sodium chloride concentration between 0.2 molar and 1 molar.

55. The process of claim 51, wherein the aqueous eluant is a saline and buffer solution suitable for human injection.

56. The process of claim 51, wherein the sodium nonatitanate is a reaction product of titanium isopropoxide and aqueous sodium hydroxide.

57. The process of claim 51, further comprising passing the rubidium-82 solution through a sodium nonatitanate filter to selectively remove any strontium-82 or strontium-85 from the solution.

58. The process of claim 57, further comprising disposing of the sodium nonatitanate filter.

59. The process of claim 51, further comprising using the rubidium-82 solution as a medical diagnostic agent or medical imaging agent.

60. The process of claim 59, further comprising injecting the rubidium-82 solution intravenously.

61. The process of claim 51, further comprising stripping strontium-82 from the sodium nonatitanate.

62. The process of claim 61, further comprising recovering the stripped strontium-82.

63. The process of claim 62, further comprising recycling the sodium nonatitanate.

64. The process of claim 51, wherein the sodium nonatitanate has not undergone hydrothermal treatment.

65. The process of claim 51 wherein the step of adjusting the pH further comprises:
   adding an acid to the solution.

66. The process of claim 51, wherein the pH is adjusted to between about 4 and about 7.5.

* * * * *

UNITED STATES PATENT AND TRADEMARK OFFICE
CERTIFICATE OF CORRECTION

| | | |
|---|---|---|
| PATENT NO. | : 7,476,377 B2 | Page 1 of 1 |
| APPLICATION NO. | : 10/894870 | |
| DATED | : January 13, 2009 | |
| INVENTOR(S) | : Teresia Moller et al. | |

It is certified that error appears in the above-identified patent and that said Letters Patent is hereby corrected as shown below:

At column 1, line 10, insert the following:

-- STATEMENT REGARDING FEDERALLY SPONSORED RESEARCH OR DEVELOPMENT

This invention was made with government support under grant number 5 R44 RR14986-03 awarded by the National Institutes of Health. The government has certain rights in this invention. --

Signed and Sealed this

Fourth Day of August, 2009

JOHN DOLL
*Acting Director of the United States Patent and Trademark Office*